(12) United States Patent
Fuller et al.

(10) Patent No.: US 10,556,072 B2
(45) Date of Patent: Feb. 11, 2020

(54) METERING DEVICE FOR A METERED DOSE INHALER

(71) Applicant: DunAn Microstaq, Inc., Austin, TX (US)

(72) Inventors: E. Nelson Fuller, Manchester, MI (US); Parthiban Arunasalam, Austin, TX (US); Joseph L. Nguyen, Austin, TX (US); Joe A. Ojeda, Austin, TX (US); Wayne C. Long, Austin, TX (US)

(73) Assignee: DunAn Microstaq, Inc., Austin, TX (US)

( * ) Notice: Subject to any disclaimer, the term of this patent is extended or adjusted under 35 U.S.C. 154(b) by 392 days.

(21) Appl. No.: 15/658,861

(22) Filed: Jul. 25, 2017

(65) Prior Publication Data
US 2018/0214646 A1 Aug. 2, 2018

Related U.S. Application Data

(60) Provisional application No. 62/452,575, filed on Jan. 31, 2017.

(51) Int. Cl.
*A61M 16/00* (2006.01)
*A61M 15/00* (2006.01)
(Continued)

(52) U.S. Cl.
CPC ........ *A61M 15/009* (2013.01); *A61M 15/002* (2014.02); *A61M 16/202* (2014.02);
(Continued)

(58) Field of Classification Search
CPC .......... A61M 15/0065; A61M 15/0066; A61M 15/0086; A61M 15/0001; A61M 15/0095;
(Continued)

(56) References Cited

U.S. PATENT DOCUMENTS 5,404,871 A * 4/1995 Goodman ............. A61M 15/00
128/200.14
6,116,234 A * 9/2000 Genova ................ A61M 11/005
128/200.14
(Continued)

FOREIGN PATENT DOCUMENTS

WO 20140209988 A1 12/2014

*Primary Examiner* — Bradley H Philips
*Assistant Examiner* — Savannah L Gabriel
(74) *Attorney, Agent, or Firm* — MacMillan, Sobanski & Todd, LLC

(57) ABSTRACT

An improved aerosol dispensing apparatus includes an aerosol container, a discharge piece, an actuator, a flow control canister valve assembly attached to the aerosol container, a battery, and an electronically controlled flow control valve electronically connected to the battery and in fluid communication with the flow control canister valve assembly. The aerosol container and the attached flow control canister valve assembly are further attached to the actuator and the actuator is mounted for slidable movement within the discharge piece. The flow control canister valve assembly is movable between an open position wherein a volume of an aerosol formulation is directed from the aerosol container through the flow control canister valve assembly to the electronically controlled flow control valve, and a closed position wherein the aerosol formulation is not permitted to flow through the flow control canister valve assembly to the electronically controlled flow control valve.

14 Claims, 10 Drawing Sheets

(51) Int. Cl.
*A61M 16/20* (2006.01)
*A61M 39/22* (2006.01)
*F16K 99/00* (2006.01)

(52) U.S. Cl.
CPC ......... *A61M 39/22* (2013.01); *F16K 99/0005* (2013.01); *F16K 99/0042* (2013.01); *A61M 2039/226* (2013.01); *A61M 2205/0244* (2013.01); *A61M 2205/3334* (2013.01); *A61M 2205/8206* (2013.01)

(58) Field of Classification Search
CPC .... A61M 15/009; A61M 11/02; A61M 11/08; B65D 83/52; F16K 99/0005
See application file for complete search history.

(56) References Cited

U.S. PATENT DOCUMENTS

| | | |
|---|---|---|
| 6,523,560 B1 | 2/2003 | Williams et al. |
| 6,540,203 B1 | 4/2003 | Hunnicutt |
| 6,845,962 B1 | 1/2005 | Barron et al. |
| 7,156,365 B2 | 1/2007 | Fuller et al. |
| 7,748,378 B2 | 7/2010 | Hodson |
| 9,328,850 B2 | 5/2016 | Fuller et al. |
| 10,125,988 B2 * | 11/2018 | Fuller ................. F23N 1/007 |
| 2009/0020114 A1 * | 1/2009 | Brambilla ........... A61M 15/009 128/200.23 |

* cited by examiner

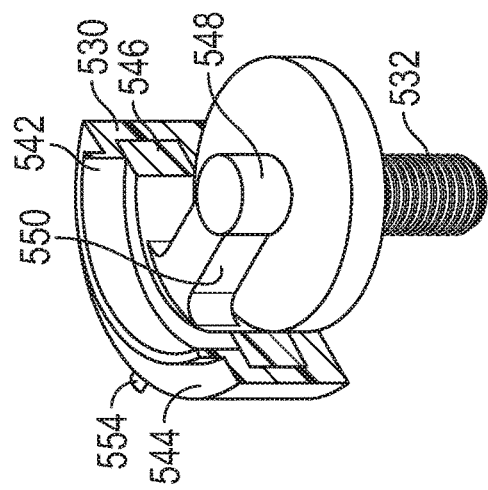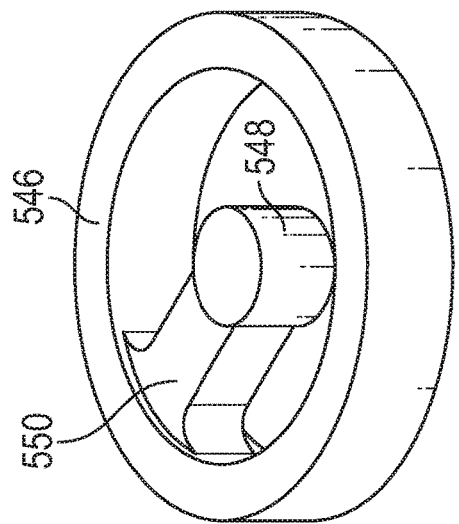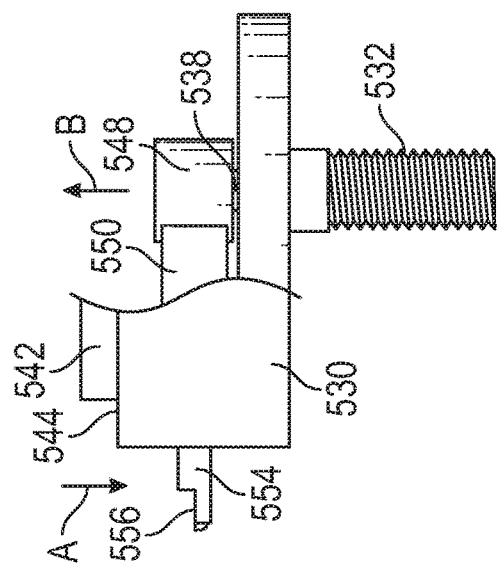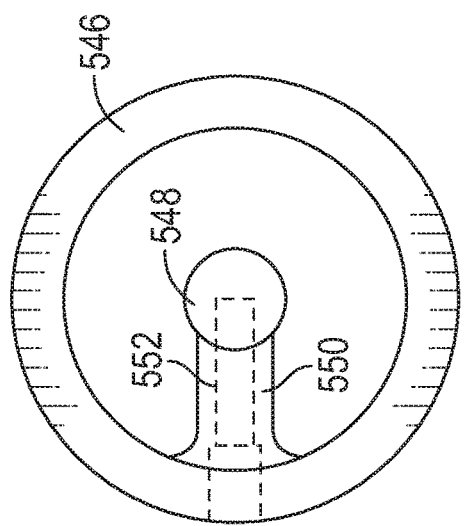

METERING DEVICE FOR A METERED DOSE INHALER

BACKGROUND OF THE INVENTION

This invention relates in general to an aerosol dispensing apparatus. In particular, this invention relates to an improved aerosol dispensing apparatus configured for use in dispensing aerosol formulations and having an improved canister metering valve and an improved canister metering valve actuator in combination with an electronically actuated microvalve.

A conventional aerosol dispensing apparatus may have a metering valve that provides a means by which aerosols are dispensed from an attached aerosol container. Such metering valves are useful for administering medicinal formulations to a patient in aerosol form.

When administering medicinal formulations, a dose of the medicinal formulation sufficient to produce a desired physiological response is delivered to the patient. It is important that a predetermined amount of the medicinal formulation be dispensed to the patient in each successive dose. Therefore, any dispensing system must be able to dispense doses of the medicinal formulation accurately, consistently, and reliably.

A metering valve may be used in an aerosol dispensing apparatus, such as a metered dose inhaler, to regulate the volume of a medicinal formulation passing from an aerosol container to a metering chamber. The metering chamber defines the maximum amount of the medicinal formulation that will be dispensed as a dose to the patient. Many aerosol dispensing apparatus rely on a controllable flow of the medicinal formulation into the metering chamber to control the accuracy and/or precision of successive metered doses of the medicinal formulation. The flow of the medicinal formulation through a conventional metering valve may become disrupted however, resulting in inconsistent or inaccurate doses of the medicinal formulation. Thus, it would be desirable to provide an improved structure for an aerosol dispensing apparatus that allows for more precise control of dosages of medicinal formulations in aerosol form.

SUMMARY OF THE INVENTION

This invention relates to an improved aerosol dispensing apparatus configured for use in dispensing aerosol formulations and having an improved canister metering valve and an improved canister metering valve actuator in combination with an electronically actuated microvalve.

In one embodiment, an improved aerosol dispensing apparatus includes an aerosol container, a discharge piece, an actuator, a flow control canister valve assembly attached to the aerosol container, a battery, and an electronically controlled flow control valve electronically connected to the battery and in fluid communication with the flow control canister valve assembly. The aerosol container and the attached flow control canister valve assembly are further attached to the actuator and the actuator is mounted for slidable movement within the discharge piece. The flow control canister valve assembly is movable between an open position wherein a volume of an aerosol formulation is directed from the aerosol container through the flow control canister valve assembly to the electronically controlled flow control valve, and a closed position wherein the aerosol formulation is not permitted to flow through the flow control canister valve assembly to the electronically controlled flow control valve.

In another embodiment, an improved flow control canister valve assembly includes a substantially cup-shaped retainer having a post aperture formed in an end wall thereof, and a pin aperture formed in a circumferentially extending wall thereof. A canister valve seat member is mounted within the retainer and has a circumferentially extending wall defining a substantially cylindrical body having an elongated mounting post extending outwardly from an outside surface of an end wall thereof and a cavity formed therein. A canister valve seal member has a substantially cylindrical body having a disc shaped closure member positioned centrally therein. The closure member is connected thereto by a transversely extending arm, and the canister valve seal member is mounted within the canister valve seat member. The canister valve seat member is mounted within the retainer such that the mounting post extends through the post aperture.

Various aspects of this invention will become apparent to those skilled in the art from the following detailed description of the preferred embodiment, when read in view of the accompanying drawings.

BRIEF DESCRIPTION OF THE DRAWINGS

FIG. 7 is an elevational view of a portion of the canister valve assembly shown in FIGS. 2, 4, 5, and 6.

FIG. 8 is a perspective view of the portion of the canister valve assembly shown in FIG. 7.

FIG. 9 is a plan view of the canister valve seal member shown in FIGS. 2, and 4 through 8.

FIG. 10 is a perspective view of the canister valve seal member shown in FIG. 9.

DETAILED DESCRIPTION OF THE PREFERRED EMBODIMENT

This invention relates to an improved structure for a canister metering valve and a canister metering valve actuator for use in dispensing aerosol formulations in an aerosol dispensing apparatus.

Referring now to FIGS. 1 through 13, a first embodiment of an improved aerosol dispensing apparatus is shown at

Figure 1:
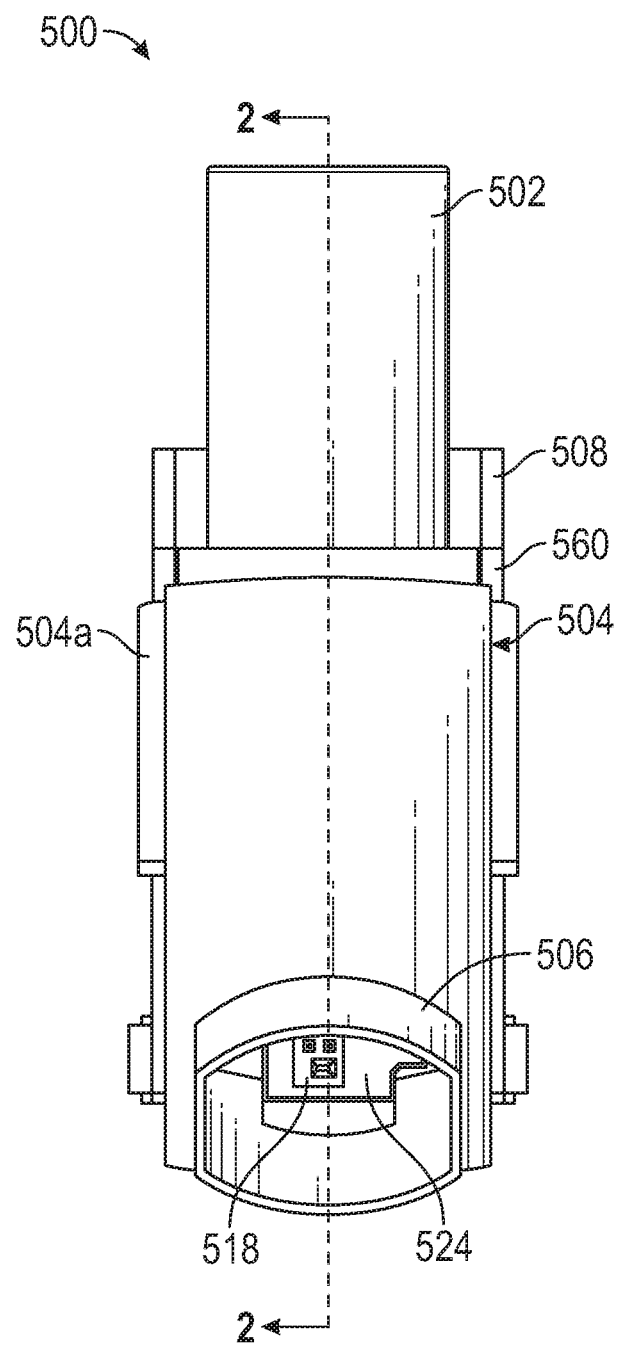
FIG. 1 a front elevational view of an improved aerosol dispensing apparatus according to this invention.
Figure 2:
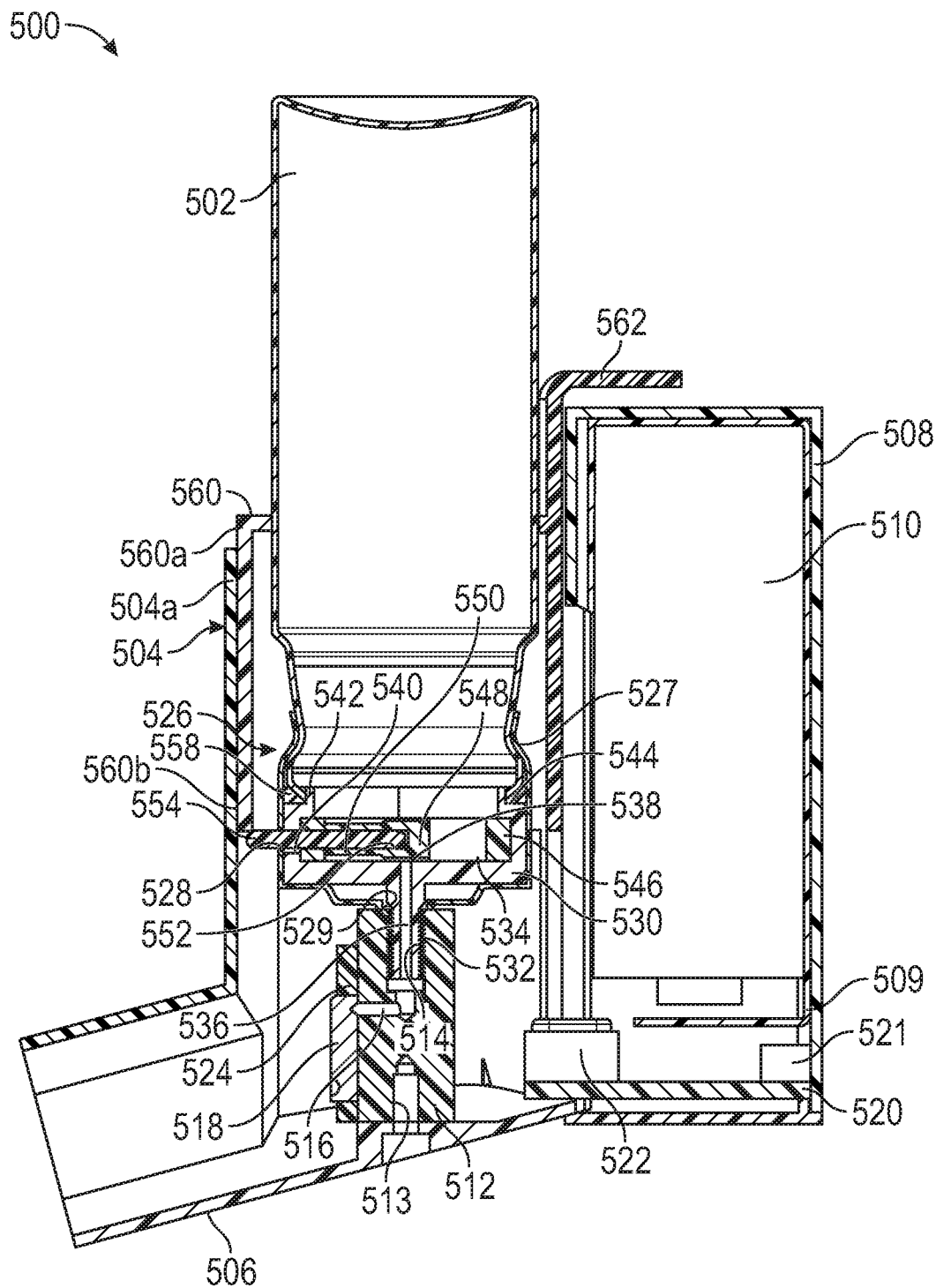
FIG. 2 is a cross-sectional view taken along the line 2-2 of FIG. 1.
Figure 3:
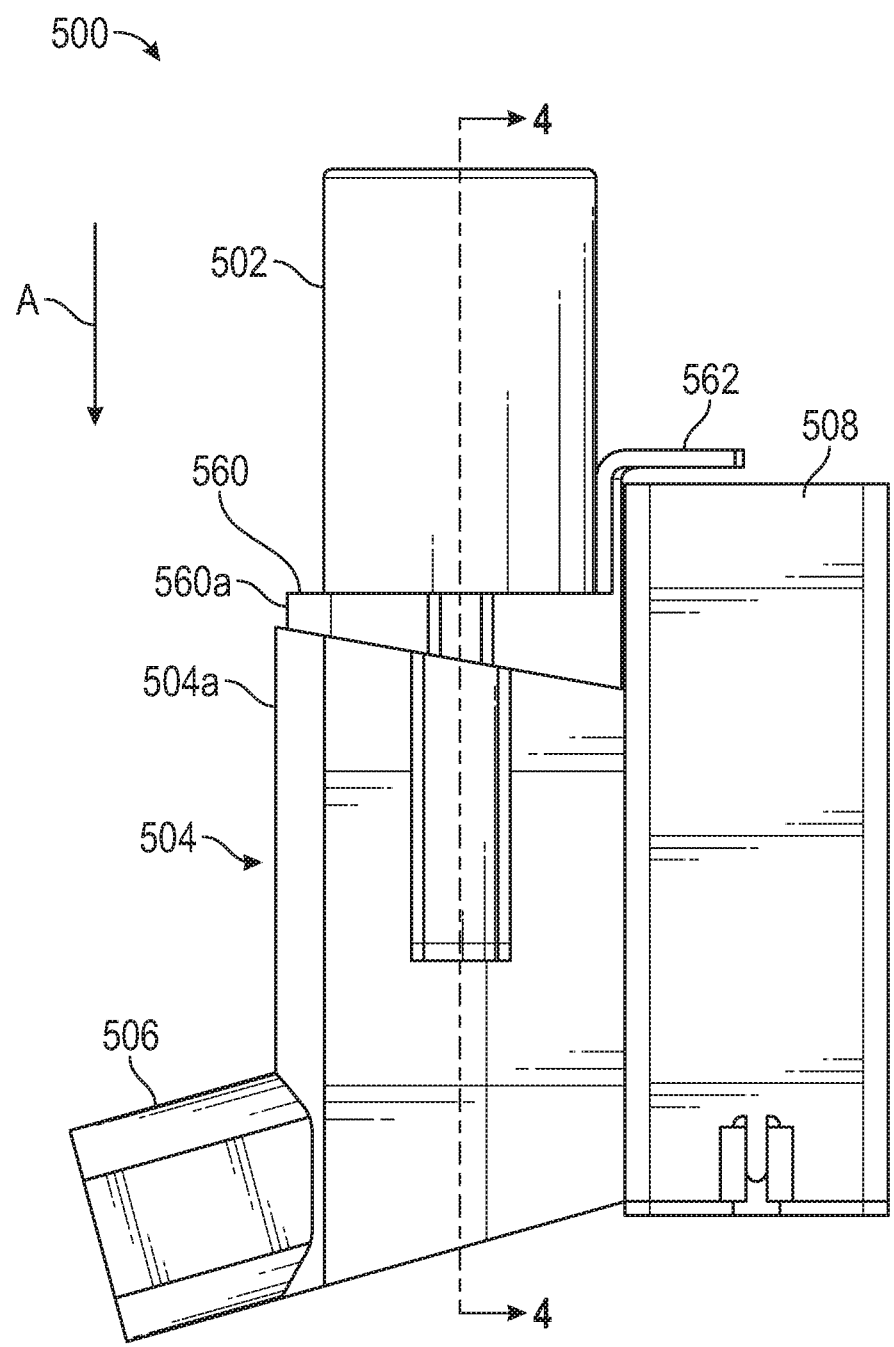
FIG. 3 a side elevational view of the improved aerosol dispensing apparatus illustrated in FIGS. 1 and 2.
Figure 4:
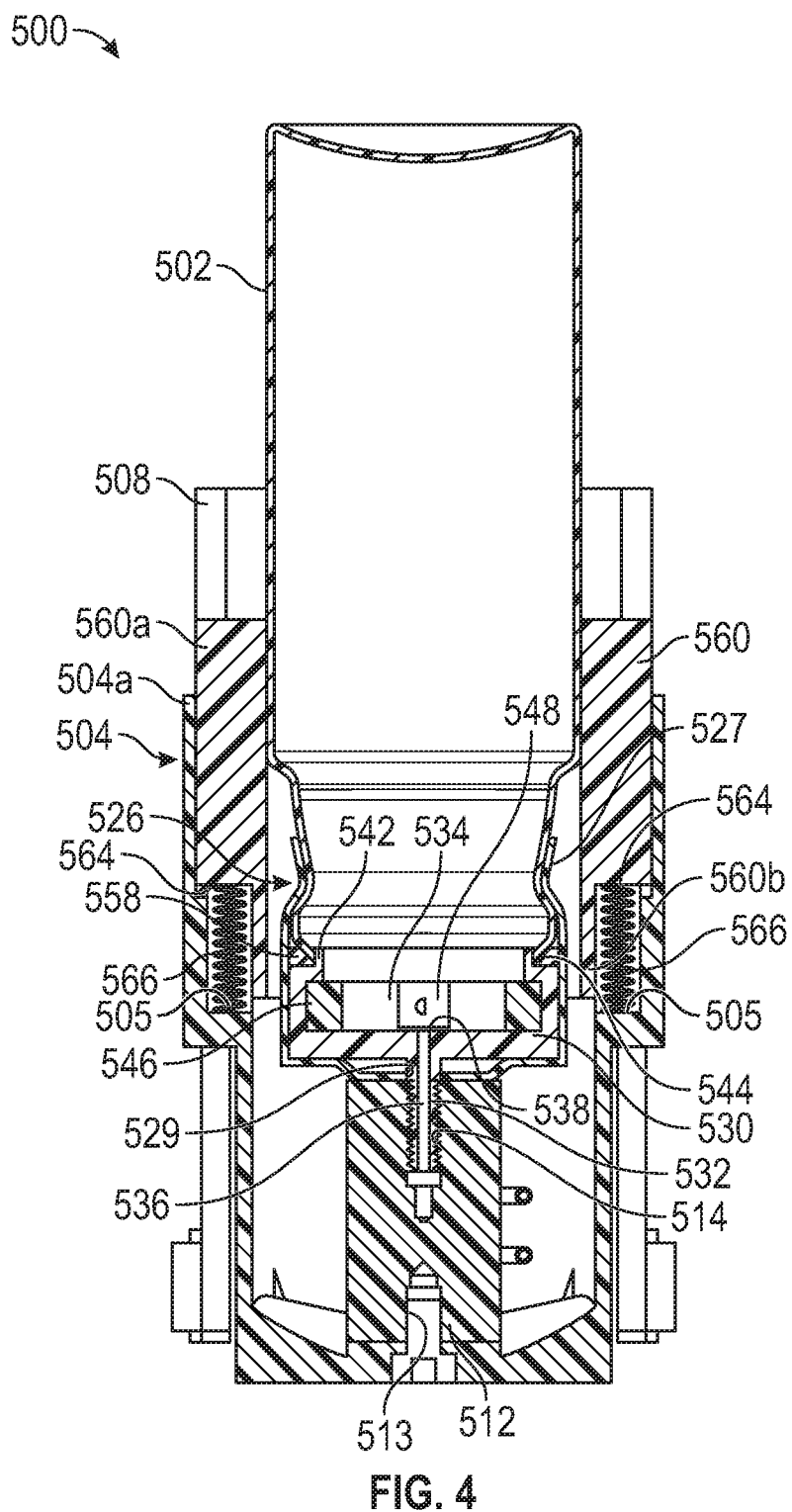
FIG. 4 is a cross-sectional view taken along the line 4-4 of FIG. 3.
Figure 6:
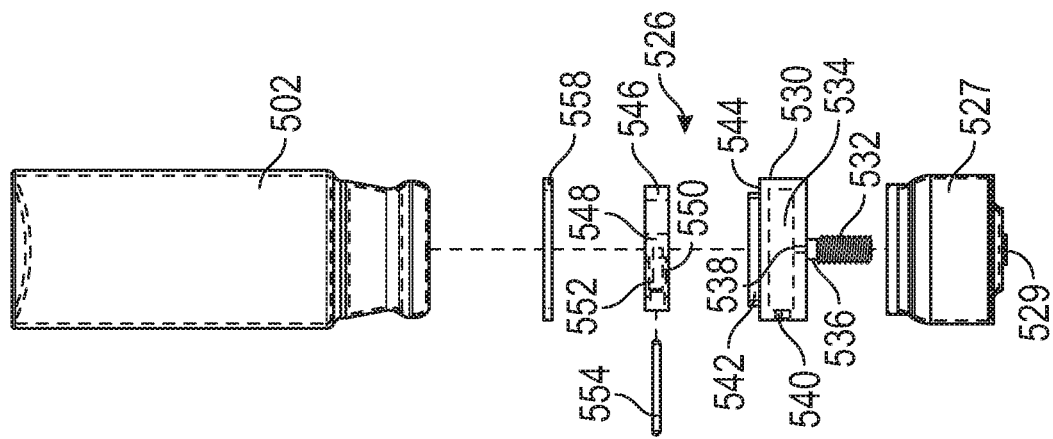
FIG. 6 is an exploded elevational view of the canister valve assembly shown in FIGS. 2, 4, and 5.
Figure 5:
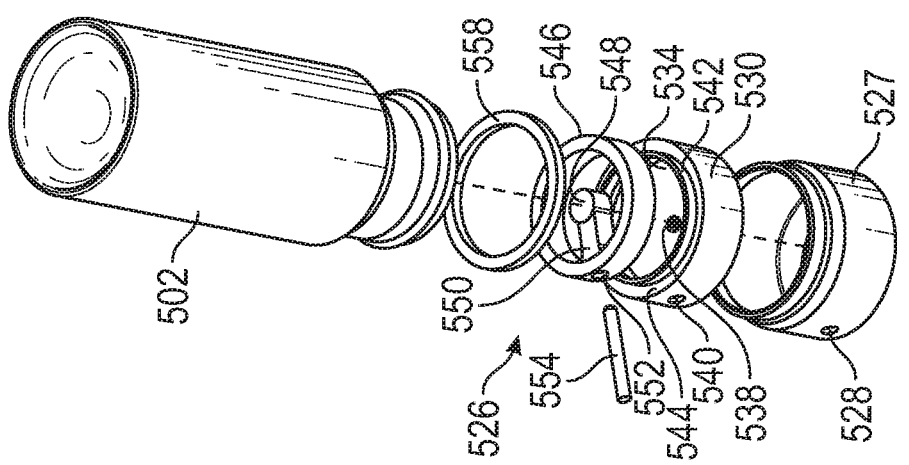
FIG. 5 is an exploded perspective view of the canister valve assembly shown in FIGS. 2 and 4.
Figure 11:
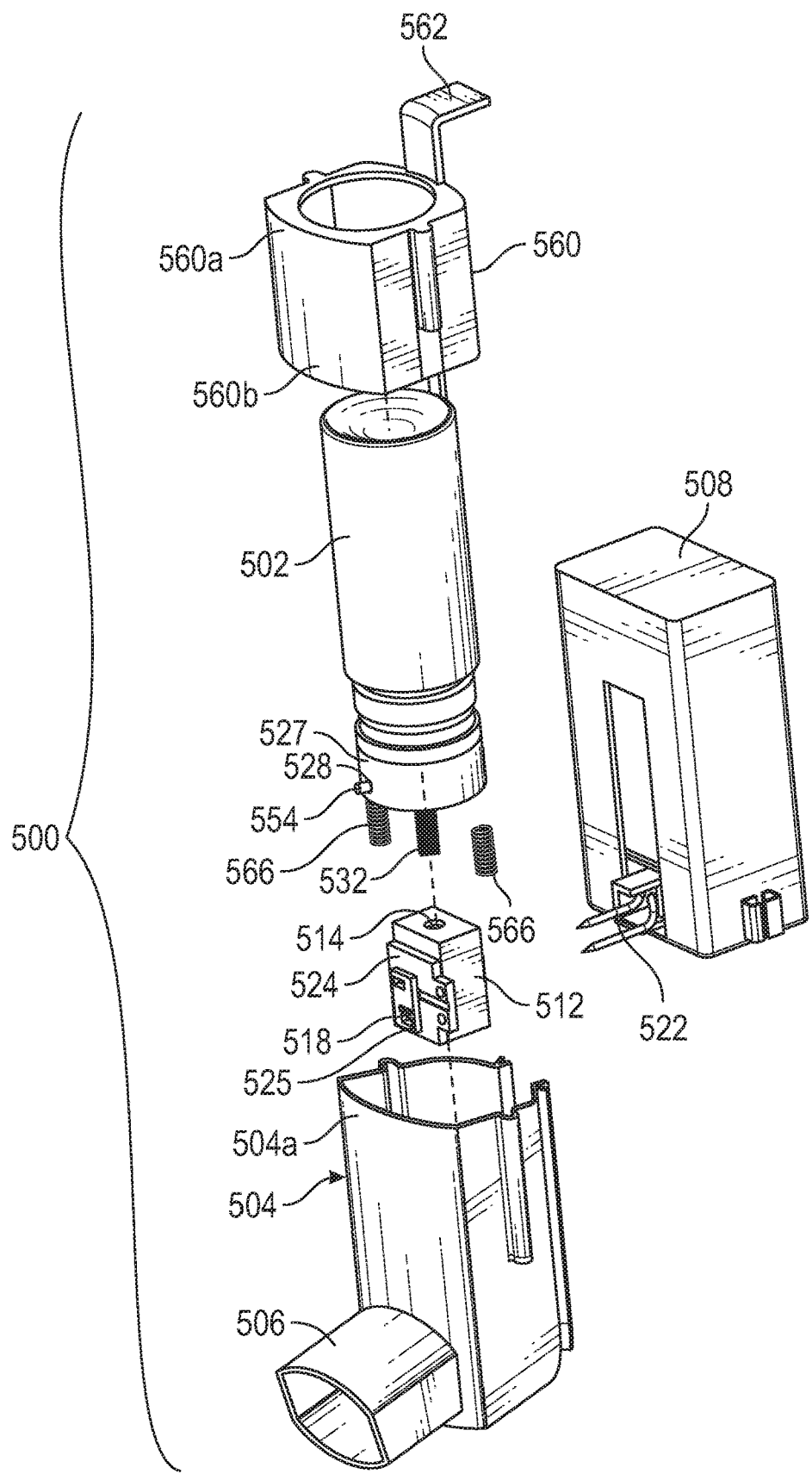
FIG. 11 is a partially exploded perspective view of the aerosol dispensing apparatus shown in FIGS. 1 through 4.
Figure 12:
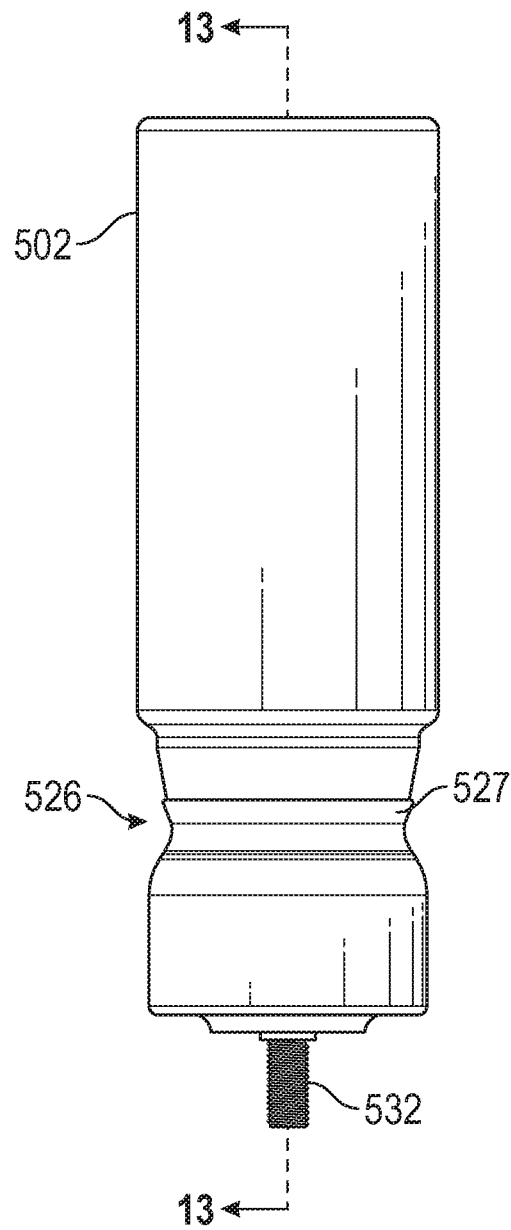
FIG. 12 is an elevational view of the canister valve assembly shown in FIGS. 1 through 6.
Figure 13:
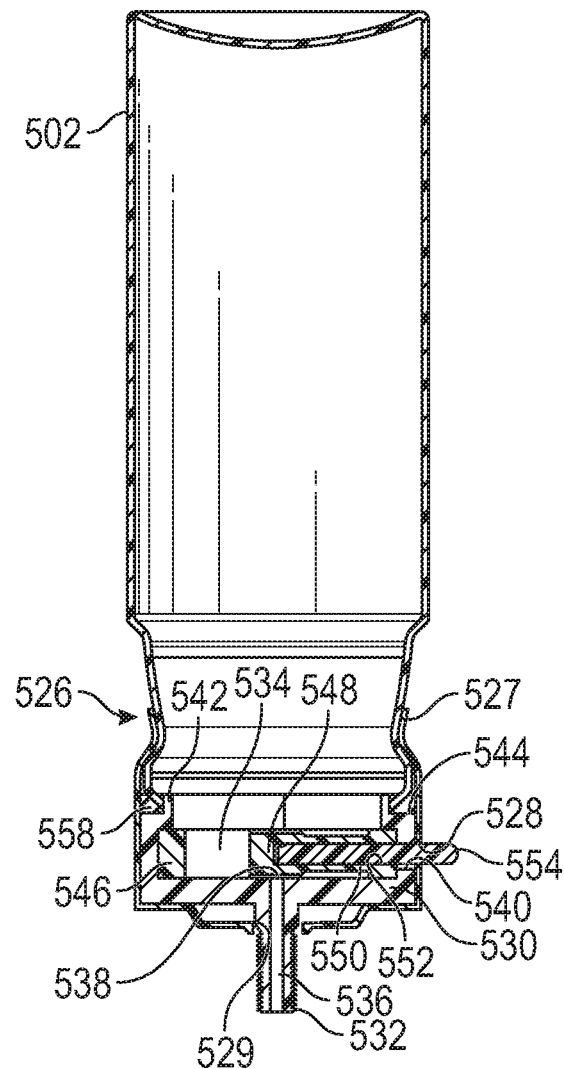
FIG. 13 is a cross-sectional elevational view taken along the line 13-13 of FIG. 12.
Figure 14:
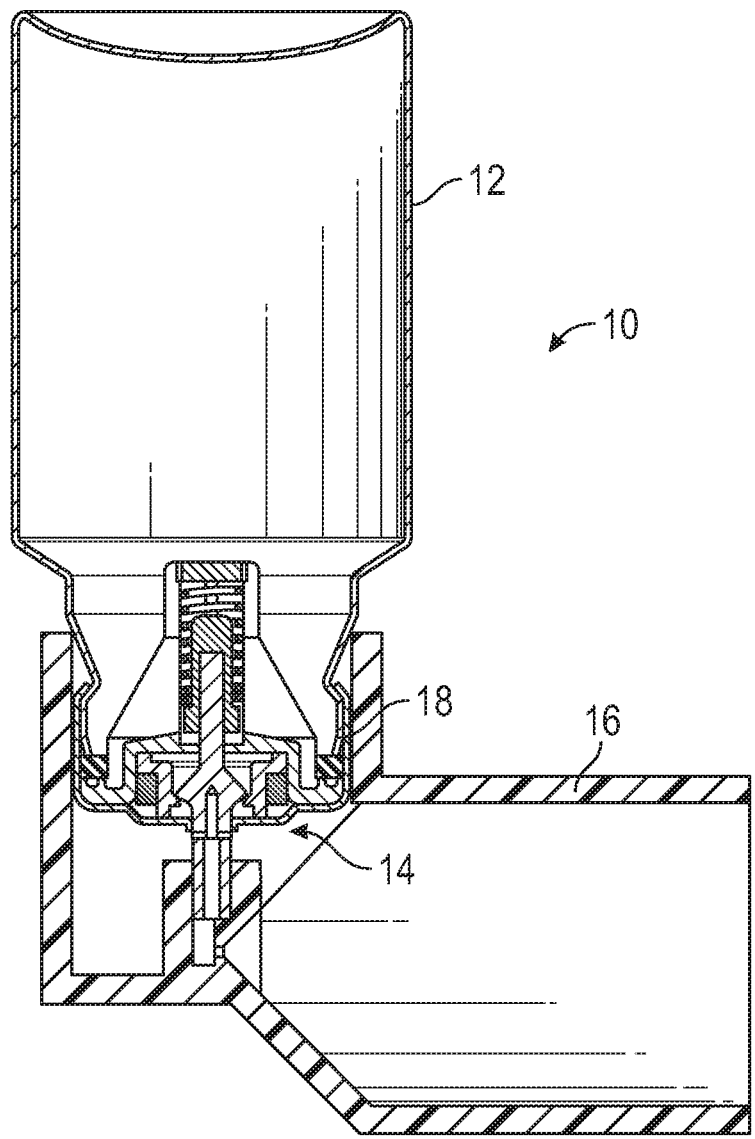
FIG. 14 is cross-sectional elevational view of a first embodiment of a known aerosol dispensing apparatus.
Figure 15:
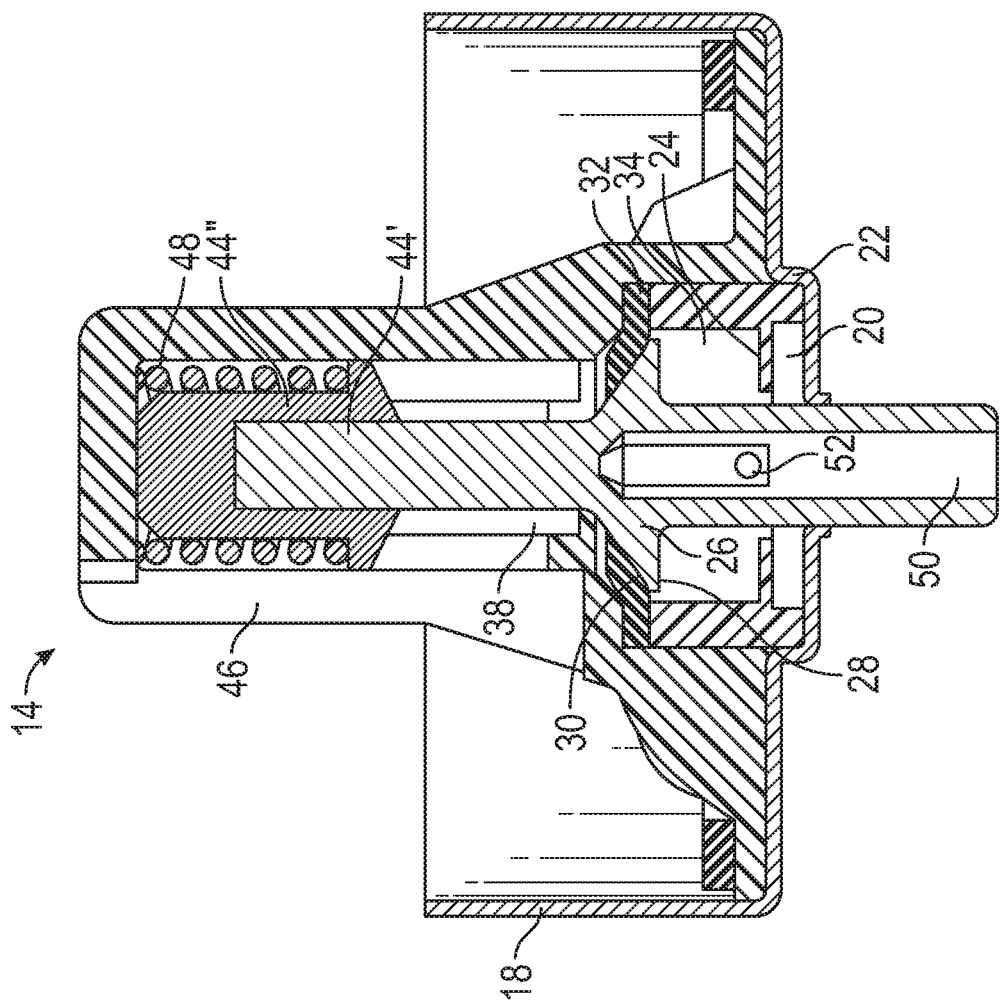
FIG. 15 is an enlarged cross-sectional elevational view of a portion of the known aerosol dispensing apparatus illustrated in FIG. 14.

500. The aerosol dispensing apparatus 500 improves on known aerosol dispensing apparatus, such as the metered dose inhaler described in U.S. Pat. No. 7,748,378 to Hodson, the disclosure of which is incorporated herein in its entirety. FIGS. 1 and 9 of U.S. Pat. No. 7,748,378 are reproduced herein as FIGS. 14 and 15, respectively. FIG. 14 for example, shows an aerosol dispensing apparatus 10 having a metering valve 14. An upper end of the metering valve 14 is crimped around the end of a conventional aerosol container 12, and a conventional discharge piece 16 is mounted around a lower end of the metering valve 14. Thus, aerosol formulation is dispensed downwardly from the aerosol container 12, through the metering valve 14, and then through the discharge piece 16 from which it is delivered to a patient. The discharge piece 16 directs the aerosol formulation toward a body cavity, such as the patient's mouth, or skin area to which the formulation is to be delivered. FIG. 15 additionally shows a seal defined between the sealing surface 30 of the valve stem 26 and the metering gasket 32 of the metering valve 14.

Figure 16:
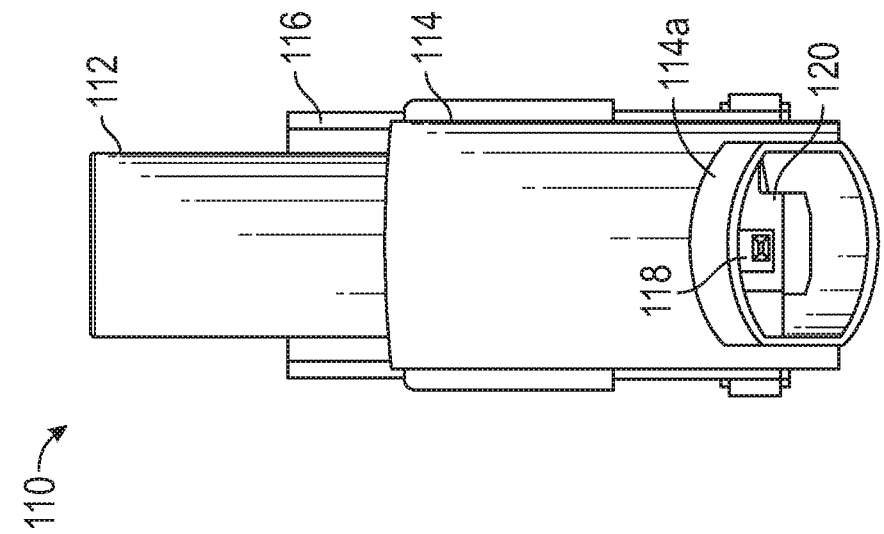
FIG. 16 is a front elevational view of a second embodiment of a known aerosol dispensing apparatus.

Another known metering valve is shown in U.S. patent application Ser. No. 14/988,139, the disclosure of which is incorporated herein in its entirety. FIG. 1 of U.S. patent application Ser. No. 14/988,139 is reproduced herein as FIG. 16. FIG. 16 illustrates an aerosol dispensing apparatus 110 that includes an aerosol container 112 mounted within a discharge piece 114. A battery housing 116 is attached to the discharge piece 14 and contains a battery (not shown). The discharge piece 114 may be configured with a mouthpiece 114a that may be inserted into the patient's mouth, thereby providing oral administration of the aerosol formulation. A microvalve 118 is mounted to a circuit board 120.

In operation, the aerosol container 112 and the discharge piece 114 may be pushed toward one another, thus allowing aerosol formulation to be dispensed from the aerosol container 112 (downwardly when viewing FIG. 16), through a metering valve (not shown), and through the microvalve 118. Aerosol formulation flow through the microvalve 118 may then be regulated and subsequently delivered through the discharge piece 114 to a patient. The discharge piece 114 directs the aerosol formulation toward the body cavity or skin area to which the formulation is to be delivered. For example, the mouthpiece 114a may be inserted into the patient's mouth, thereby providing oral administration of the aerosol formulation.

The aerosol dispensing apparatus 110 disclosed in U.S. patent application Ser. No. 14/988,139 improves on the metering valve 14 of U.S. Pat. No. 7,748,378. For example, the seal defined between the sealing surface 30 and the metering gasket 32 of the metering valve 14 in FIG. 9 of U.S. Pat. No. 7,748,378 (and FIG. 15 herein) is not needed in the aerosol dispensing apparatus 110 disclosed in U.S. patent application Ser. No. 14/988,139, and shown in FIG. 16 herein, thus allowing a continuous flow of aerosol formulation to be dispersed when the canister 112 of the aerosol dispensing apparatus 110 is depressed. This flow of aerosol formulation may then be regulated by the flow control valve or electronically actuated microvalve 118. The microvalve 118 may be controlled by a battery, a contact switch, and other support electronics (not shown).

Advantageously, the improved aerosol dispensing apparatus 500 illustrated in FIGS. 1 through 13 allows the amount and duration of aerosol dispersant distribution to be modified as required by a given treatment.

The aerosol dispensing apparatus 500 includes an aerosol container 502 mounted within a discharge piece 504. The discharge piece 504 includes a first portion 504a (the upper portion when viewing FIGS. 1 and 2) defining a substantially cylindrical inside surface. As best shown in FIG. 4, a plurality of spring seats 505 are formed in the inside surface of the first portion 504*a* of the discharge piece 504. The discharge piece 504 may be configured with a mouthpiece 506 that may be inserted into the patient's mouth, thereby providing oral administration of an aerosol formulation. A battery housing 508 may be attached to the discharge piece 504 and may contain a battery 510, not shown in section in FIG. 2.

A valve block 512 may be mounted to an inside surface of the discharge piece 504 by any desired means, such as by one or more threaded fasteners (not shown) attached within a fastener aperture 513, or with an adhesive. The valve block 512 includes an axially extending bore 514 formed therein. The axially extending bore 514 terminates at a transverse fluid passageway 516 that is in fluid communication with an electronically actuated flow control or metering valve mounted to an outside surface of the valve block 512. In the illustrated embodiment, the metering valve is an electronically actuated microvalve 518, the structure and function of which is described below. Alternatively, the metering valve may be any relatively small, i.e., configured to fit within the discharge piece 504, electronically controlled flow control valve, such as a solenoid valve.

The battery 510 disposed within the battery housing 508 may be any conventional rechargeable or non-rechargeable battery. The battery 510 may be mounted within a conventional battery mount 509. A first electronic circuit board 520 may also be mounted within the battery housing 508. The battery 510 may be connected to the first electronic circuit board 520 by conventional electrical connectors (not shown). The first electronic circuit board 520 may have a microcontroller 521, a communications or charging port (not shown), an actuator switch 522, and any other desired control electronics (not shown) for controlling the microvalve 518. Access openings (not shown) may be formed in the battery housing 508 to provide access to the charging port (not shown) and the actuator switch 522.

As shown in FIGS. 1, 2 and 11, a second circuit board 524 is mounted to an outside surface of the valve block 512. The second circuit board 524 may include a microvalve mounting aperture 525 (best shown in FIG. 11) formed therein. Thus, the microvalve 518 may be mounted within the microvalve mounting aperture 525 and to an outside surface of the valve block 512, and is in fluid communication with the transverse fluid passageway 516. Additional electrical connectors, such as electrical wires (not shown), extend between the first and second circuit boards 520 and 524.

The microvalve 518 is electrically connected to the second circuit board 524 in a conventional manner, such as with electrical wires (not shown). As described in detail below in the description of the microvalve 518, such electrical wires (not shown) may extend from the second circuit board 524 through electrical ports, such as electrical ports 411, to bond pads 407*a* on the intermediate plate 403, as shown in detail in U.S. patent application Ser. No. 14/988,139, for passing an electrical current the microvalve 518.

As best shown in FIGS. 2, 4 through 6, 11, and 13, a flow control canister valve assembly is shown at 526. The canister valve assembly 526 is configured as an on-off valve and includes a substantially cup-shaped retainer 527. The retainer 527 includes a post aperture 529 formed in an end wall thereof, and a pin aperture 528 formed in a circumferentially extending wall thereof. A canister valve seat member 530 includes a substantially cylindrical body having an elongated mounting post 532 extending outwardly there-from (downwardly when viewing FIGS. 2, 4, and 6), and a cavity 534 formed therein. An axially extending fluid passageway 536 is formed in the mounting post 532 and extends from the cavity 534 to a distal end of the mounting post 532. An opening of the fluid passageway 536 in the cavity 534 defines a valve seat 538. If desired, the valve seat 538 may extend outwardly from an inside end wall of the canister valve seat member 530 (upwardly when viewing FIGS. 2, 4, and 6), such as to define an annular valve seat (not shown). A pin aperture 540 extends transversely through a circumferentially extending wall of the canister valve seat member 530. A circumferentially extending lip 542 is formed on an end wall of the canister valve seat member 530 (the upper end when viewing FIGS. 2, 4, and 6) and defines a circumferentially extending shoulder 544. The canister valve seat member 530 is mounted within the retainer 527 such that the mounting post 532 extends through the post aperture 529.

As shown in FIGS. 2, 4 through 9, and 13, a canister valve seal member 546 includes a substantially cylindrical body having a disc shaped closure member 548 positioned centrally therein and connected thereto by a transversely extending arm 550. An axially extending pin bore 552 is formed through the arm 550. An elongated actuator pin 554 is mounted within the pin bore 552 and secured therein by any desired means, such as with an adhesive, by press-fit, and by over-molding. A notch 556 may be formed in a distal end of the actuator pin 554. The canister valve seal member 546 is mounted within the cavity 534 of the canister valve seat member 530 such that the closure member 548 is positioned on the valve seat 538, and such that the actuator pin 554 extends through the pin apertures 540 and 528. An annular seal, such as an O-ring 558 is disposed on the shoulder 544 of the canister valve seat member 530. Alternatively, the annular seal may be any other conventional annular seal.

An open end of the aerosol container 502 is seated about the circumferentially extending lip 542 of the canister valve seat member 530 and the open end 528a of the retainer 527 may be attached to the open end of the aerosol container 502 such as by crimping. Alternatively, the retainer 527 may be attached to the aerosol container 502 by other means, such as with an adhesive, with a laser weld, and with an electronic beam weld. The mounting post 532 may be attached within the bore 514 of the valve block 512 by any means, such as the illustrated threaded connection.

The arm 550 is flexible or semi-flexible as described below, and may be formed from EPDM rubber. Alternatively, the arm 550 may be formed from any desired elastomer and other flexible and semi-flexible materials.

An actuator 560 is substantially cylindrical and has a first end 560*a* (the upper end when viewing FIGS. 2 and 4) and a second end 560*b* (the lower end when viewing FIGS. 2 and 4). A stop flange 562 extends radially outwardly from the first end 560*a* such that it extends over the battery housing 508. The aerosol container 502 is attached within the open first end 560*a* of the actuator 560, and the actuator 560 is slidably mounted within the discharge piece 504. As best shown in FIG. 4, a plurality of spring seats 564 is formed in an outer surface of the actuator 560.

The aerosol container 502 and the retainer 527 may be formed from aluminum. Alternatively, the aerosol container 502 and the retainer 527 may be formed from any desired metal, metal alloy, and non-metal material. The actuator pin 554 may be formed from stainless steel. Alternatively, the actuator pin 554 may be formed from any desired metal, metal alloy, and non-metal material. The canister valve seal member 546 and the O-ring 558 may be formed from EPDM rubber. Alternatively, the canister valve seal member 546 and the O-ring 558 may be formed from any desired elastomer. The canister valve seat member 530 may be formed from aluminum. Alternatively, the canister valve seat member 530 may be formed from any desired metal, metal alloy, and non-metal material. Non-limiting examples of such alternative non-metal materials include nylon and polymers such as Polyethylene Terephthalate (PET), High-Density Polyethylene (HDPE), Polypropylene Copolymer, and Polytetrafluoroethylene (PTFE).

Springs 566 are disposed between each pair of spring seats 564 and spring seats 505 such that the springs 566 urge the actuator 560 away from the discharge piece 504.

To operate the improved aerosol dispensing apparatus 500, a user may urge the aerosol container 502 and the attached actuator 560 into the discharge piece 504 (downwardly when viewing FIGS. 3 and 7). The actuator 560 contacts the notch 556 in the actuator pin 554 to urge the actuator pin 554 toward the mouthpiece 506 (downwardly in the direction of the arrow A when viewing FIGS. 3 and 7) and to further urge the closure member 548 off of the valve seat 538 (upwardly in the direction of the arrow B when viewing FIG. 7), thus allowing aerosol formulation to flow from the aerosol container 502 to the microvalve 518.

The downward movement of the aerosol container 502 and the attached actuator 560 also simultaneously activates the actuator switch 522, thus actuating the microvalve 518 such that aerosol formulation flow through the microvalve 518 may be optimally regulated and subsequently delivered through the discharge piece 504 to the patient or other desired location.

Thus, when the improved aerosol dispensing apparatus 500 is actuated by the user, a continuous flow of aerosol formulation travels through the canister valve assembly 526 to the microvalve 518. The flow of aerosol formulation through the microvalve 518, and therefore the dose amount of aerosol formulation dispersant dispensed thereby, may then be very precisely controlled by the microcontroller 521 as required for a desired treatment.

It has been shown that a force of about 0.1 N on the actuator pin 554 is sufficient to open the valve seat 538; i.e. to move the closure member 548 away from the valve seat 538 by distance of about 0.4 mm. A fluid pressure force within the range of about 1.8 N to about 3.0 N and a spring force of about 1.8 N combine to make the total actuation force required to open the valve seat 538 and activate the actuator switch 522 within the range of about 4 N to about 5 N. This force of about 4 N to about 5 N is significantly lower than the range of about 22 N to about 25 N force required to actuate conventional metering valves in conventional aerosol dispensing apparatus.

The microcontroller 521 may include an algorithm that moves the microvalve 518 between open and closed positions to ensure optimal dispersal of the aerosol formulation to a user. For example, by selectively moving the microvalve 518 between open and closed positions, the microcontroller 521 may precisely control dosage volume and/or the duration of an aerosol formulation dose through the microvalve 518. An optimal dosage volume and an optimal duration of an aerosol formulation dose will vary based on factors including the type of medication being dispersed, the age of the user, and the like, and may be determined by routine experimentation.

The microcontroller 521 may also include an algorithm with a counter function configured to count the number of doses administered in a given period, such as the elapsed time since the most recent previous aerosol container 502 change. The microcontroller 521 may also be programmed as needed by a physician or a pharmacist via the communications port (not shown).

Advantageously, the canister valve assembly 526 of the aerosol dispensing apparatus 500 is simpler and easier to operate than the valves in conventional aerosol dispensing apparatus while allowing precise control of the aerosol formulation being dispersed.

The canister valve assembly 526 has been described and illustrated herein as a component of the aerosol dispensing apparatus 500. It will be understood however, that the canister valve assembly 526 may be used in applications other than an aerosol dispensing apparatus, such as for example, any device or mechanism that would benefit from a valve that is simple, easy to operate, and allows precise control of a fluid flowing therethrough.

Micro Electro Mechanical Systems (MEMS) are a class of systems that are physically small, having features with sizes in the micrometer range; i.e., about 10 µm or smaller. These systems have both electrical and mechanical components. The term "micromachining" is commonly understood to mean the production of three-dimensional structures and moving parts of MEMS devices. MEMS originally used modified integrated circuit (computer chip) fabrication techniques (such as chemical etching) and materials (such as silicon semiconductor material) to micromachine these very small mechanical devices. Today, there are many more micromachining techniques and materials available. The term "micromachined device" as used in this application means a device having some features with sizes of about 10 µm or smaller, and thus by definition is at least partially formed by micromachining. More particularly, the term "microvalve" as used in this application means a valve having features with sizes of about 10 µm or smaller, and thus by definition is at least partially formed by micromachining. The term "microvalve device" as used in this application means a micromachined device that includes a microvalve, and that may include other components. It should be noted that if components other than a microvalve are included in the microvalve device, these other components may be micromachined components or standard sized (larger) components. Similarly, a micromachined device may include both micromachined components and standard sized (larger) components.

Various microvalve devices have been proposed for controlling fluid flow within a fluid circuit. A typical microvalve device includes a displaceable member or valve component movably supported by a body for movement between a closed position and a fully open position. When placed in the closed position, the valve component substantially blocks or closes a first fluid port that is otherwise in fluid communication with a second fluid port, thereby substantially preventing fluid from flowing between the fluid ports. When the valve component moves from the closed position to the fully open position, fluid is increasingly allowed to flow between the fluid ports.

U.S. Pat. Nos. 6,523,560, 6,540,203, and 6,845,962, the disclosures of which are incorporated herein by reference, describe microvalves made of multiple layers of material. The multiple layers are micromachined and bonded together to form a microvalve body and the various microvalve components contained therein, including an intermediate mechanical layer containing the movable parts of the microvalve. The movable parts are formed by removing material from an intermediate mechanical layer (by known micromachined device fabrication techniques, such as, but not limited to, Deep Reactive Ion Etching) to create a movable valve element that remains attached to the rest of the part by a spring-like member. Typically, the material is removed by creating a pattern of slots through the material to achieve the desired shape. The movable valve element will then be able to move in one or more directions an amount roughly equal to the slot width.

Although the surface area of the intermediate mechanical layer in each of the microvalves disclosed in U.S. Pat. Nos. 6,523,560, 6,540,203, and 6,845,962 is relatively small, e.g. about 52 mm$^2$, it is desirable to provide an intermediate mechanical layer for a microvalve having an even smaller surface area.

One embodiment of a microvalve device suitable for use with the invention is described in U.S. Pat. No. 9,328,850 to Fuller et al. published Dec. 25, 2014 and incorporated in its entirety herein.

The principle and mode of operation of the invention have been described in its preferred embodiment. However, it should be noted that the invention described herein may be practiced otherwise than as specifically illustrated and described without departing from its scope.

The invention claimed is:

1. An aerosol dispensing apparatus comprising:
 an aerosol container;
 a discharge piece;
 an actuator;
 a flow control canister valve assembly attached to the aerosol container, and including a substantially cup-shaped retainer, a canister valve seat member mounted within the retainer, and a canister valve seal member mounted within the canister valve seat member;
 wherein the retainer includes a post aperture formed in an end wall thereof, and a pin aperture formed in a circumferentially extending wall thereof;
 a battery; and
 an electronically controlled flow control valve electronically connected to the battery and in fluid communication with the flow control canister valve assembly;
 wherein the aerosol container and the attached flow control canister valve assembly are further attached to the actuator and the actuator is mounted for slidable movement within the discharge piece; and
 wherein the flow control canister valve assembly is movable between an open position wherein a volume of an aerosol formulation is directed from the aerosol container through the flow control canister valve assembly to the electronically controlled flow control valve, and a closed position wherein the aerosol formulation is not permitted to flow through the flow control canister valve assembly to the electronically controlled flow control valve.

2. The aerosol dispensing apparatus according to claim 1, wherein the electronically controlled flow control valve is an electronically actuated microvalve.

3. The aerosol dispensing apparatus according to claim 1, wherein the canister valve seat member includes a circumferentially extending wall defining a substantially cylindrical body having an elongated mounting post extending outwardly from an outside surface of an end wall thereof and a cavity formed therein.

4. The aerosol dispensing apparatus according to claim 3, wherein the canister valve seat member further includes an axially extending fluid passageway formed in the mounting post and extending from the cavity to a distal end of the mounting post.

5. The aerosol dispensing apparatus according to claim 4, wherein an opening of the fluid passageway in the cavity defines a valve seat.

6. The aerosol dispensing apparatus according to claim 5, wherein the valve seat extends outwardly from an inside surface of the end wall of the canister valve seat member such as to define an annular valve seat.

7. The aerosol dispensing apparatus according to claim 5, wherein a pin aperture extends transversely through the circumferentially extending wall of the canister valve seat member.

8. The aerosol dispensing apparatus according to claim 7, wherein a circumferentially extending lip is formed on an open end of the circumferentially extending wall and defines a circumferentially extending shoulder.

9. The aerosol dispensing apparatus according to claim 3, wherein the canister valve seat member is mounted within the retainer such that the mounting post extends through the post aperture.

10. The aerosol dispensing apparatus according to claim 8, wherein the canister valve seal member includes a substantially cylindrical body having a disc shaped closure member positioned centrally therein, the closure member connected thereto by a transversely extending arm.

11. The aerosol dispensing apparatus according to claim 10, wherein an axially extending pin bore is formed through the arm.

12. The aerosol dispensing apparatus according to claim 11, wherein an elongated actuator pin is mounted within the pin bore.

13. The aerosol dispensing apparatus according to claim 12, wherein the actuator pin has a notch formed in a distal end thereof.

14. The aerosol dispensing apparatus according to claim 13, wherein the canister valve seal member is mounted within the cavity of the canister valve seat member such that the closure member is positioned on the valve seat, and such that the actuator pin extends through the pin apertures of the canister valve seat member and the retainer, respectively.

* * * * *